(12) United States Patent
Molino et al.

(10) Patent No.: US 7,956,218 B2
(45) Date of Patent: Jun. 7, 2011

(54) ORGANIC SALTS OF β-ALANINE

(75) Inventors: Michele Molino, Mississauga (CA); Joseph MacDougall, Mississauga (CA)

(73) Assignee: Northern Innovations and Formulations Corp., Oakdale (CA)

( * ) Notice: Subject to any disclaimer, the term of this patent is extended or adjusted under 35 U.S.C. 154(b) by 278 days.

(21) Appl. No.: 11/954,644

(22) Filed: Dec. 12, 2007

(65) Prior Publication Data
US 2009/0156676 A1    Jun. 18, 2009

(51) Int. Cl.
*C07C 229/08* (2006.01)
(52) U.S. Cl. ...................................................... 562/576
(58) Field of Classification Search .................. None
See application file for complete search history.

(56) References Cited

FOREIGN PATENT DOCUMENTS
WO    WO 2007/073398    *    6/2007

OTHER PUBLICATIONS

Berge et al. Journal of Pharmaceutical Sciences, 1977, 66, No. 1, p. 1-19.*
Cooke R, et al. The effects of ADP and phosphate on the contraction of muscle fibers. Biophys J. Nov. 1985; 485(5):789-98.
Febbraio Ma, et al. Skeletal muscle energy metabolism during prolonged, fatiguing exercise. J Appl Physiol. Dec. 1999; 87(6):2341-7.
Bate-Smith EC. The buffering of muscle in rigour: protein, phosphate, and carnosine. J Physiol. 1938;92:336-43.
Fitzgerald, M.A., et al., "Some Organic Salts of Glycine, the Alanines and dl-Leucine" Proceedings and Transaction of the Royal Society of Canada (1937), 31, III, 153-157.
Rajagopal, K., et al., "β-Alaninium trichloraceteate at 105K" Acta Crystallographica (2003), E59, 206-208.
Nishijo, J., et al., "The Solid Complex of Aminomalonic Acid with β-Alanine and its Thermal Decomposition" Bulletin of the Chemical Society of Japan, vol. 45, 2070-2074 (1972).
Rajagopal, K., et al., "β-Alaninium meleate" Acta Crystallographica (2001), E57, 922-924.
Krishnakumar, R.V., et al., "β-Alaninium oxalate hemihydrate", Acta Crystallographica (2002), E58, 117-119.
International Search Report for PCT/CA2007/002264.

* cited by examiner

*Primary Examiner* — Daniel M Sullivan
*Assistant Examiner* — Yevegeny Valenrod

(57) ABSTRACT

The present invention relates to stable salts of β-alanine and an organic acid endowed with enhanced nutritional and/or therapeutical efficacy in respect to their individual effects and to solid compositions containing such salts, particularly suited to oral administration. A method of preparation is also provided.

13 Claims, No Drawings

ORGANIC SALTS OF β-ALANINE

FIELD OF THE INVENTION

The present invention relates to a structure and method for producing stable salts of β-alanine and organic acids. More specifically, formed salts of the present invention are particularly well suited for oral administration thereby the formed salts may provide enhanced nutritional and/or therapeutical efficacy in relation to the individual components alone.

BACKGROUND OF THE INVENTION

It is commonly known that increased muscle mass, strength and extended muscular performance occur in the most effective manner when exercise routines are done to complete exhaustion. However, during extended periods of exercise, metabolites from the breakdown of adenosine triphosphate (ATP), mainly hydrogen ions ($H^+$), begin to accumulate leading to a decline in the pH levels of blood and muscle, which can be problematic or undesirable. The increase in acidity of the muscle, as a result of the accumulation of $H^+$ ions, is directly linked to muscle fatigue, which ultimately causes a decrease in the duration of intensive bouts of exercise (Cooke R, Pate E. The effects of ADP and phosphate on the contraction of muscle fibers. Biophys J. 1985 November; 48(5):789-98). This fatigue is a result of inhibition of enzymes, by decreased pH, which are vital for energy production and the force-producing capacity of muscles (Febbraio M A, Dancey J. Skeletal muscle energy metabolism during prolonged, fatiguing exercise. J Appl Physiol. 1999 December; 87(6):2341-7).

Carnosine is one of the most effective buffers, or pH stabilizers, in human skeletal muscle, and as such is very efficient at mopping up excess $H^+$ ions. When carnosine is ingested as food, it must be broken down to its constituent amino acids (β-alanine and histidine) in order cross cell membranes, after which it is then reassembled. Due to lack of absorption, in addition to the financial cost of the raw material, carnosine, administration of the constituent amino acids has been explored. For example, administration of exogenous β-alanine has been shown to increase the levels of carnosine in skeletal muscle cells (Bate-Smith E C. The buffering of muscle in rigour: protein, phosphate, and carnosine. J Physiol. 1938; 92:336-43).

Additionally, other methods for increasing the duration of exercise have been explored. One such method is the administering of compounds that are essential for ATP synthesis and are depleted during exhaustive exercise, such as malic acid. Malic acid is a naturally occurring compound found in a large number of fruits and vegetables, as well as all living cells; which plays a key role in the transportation of NADH from the cytosol to the mitochondria for energy production (ATP production). Malic acid is part of the initiation of the Krebs cycle and is one of the only metabolites that actually decrease in concentration during exercise. Thus, administration of exogenous malic acid will result in increased ATP production as a result of attenuation of malic acid depletion.

Supplementation with other deprotonated organic acids can be used for attenuation of metabolic acidosis. For example, citrate lacks all of its acidic protons, yielding three carboxylate functionalities that can readily take up free protons. Since all of acidic protons are removed, the citrate has three sites which are capable of taking up free protons in serum and working muscle. Therefore, administration of deprotonated organic acids can inhibit the decrease in pH, which is a result of ATP hydrolysis, thereby leading to less fatigue resulting from the inhibition of enzymes that are vital for energy production and the force-producing capacity of muscles.

SUMMARY OF THE INVENTION

In the present invention, compounds and methods for their production are disclosed. Specifically, the compounds are salts comprising an organic acid and β-alanine, and having a structure of Formula 1:

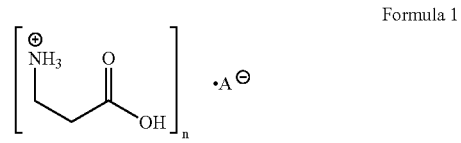

Formula 1 wherein:
$A^-$ represents a deprotonated organic acid selected from the group consisting of: malate, citrate and fumarate; and
where $A^-$ is malate or fumarate, n=2, and
where $A^-$ is citrate; n=3.

DETAILED DESCRIPTION OF THE INVENTION

In the following description, for the purposes of explanations, numerous specific details are set forth in order to provide a thorough understanding of the present invention. It will be apparent, however, to one of ordinary skill in the art that the present invention may be practiced without these specific details.

The present invention is directed towards the structures and synthesis of salts of β-alanine and organic acids.

The present invention provides for the production of stable salts, which may afford a combination of β-alanine and an organic acid, free of physiologically unsafe additives to an individual upon administration to said individual. Furthermore, the present invention is particularly well suited for use in tablets, capsules, powders, granules, powdered beverage mixes and other forms known in the art of dietary supplements.

β-alanine combined with an organic acid forms a non-hygroscopic crystalline powder, which is stable in storage and can be processed without special precautions. Due to the non-hygroscopic nature of the β-alanine salt it would be understood by one of skill in the art, that the salt is easy to process and is particularly suitable for processing with rapidly running machines, since it does not tend to stick together or become lumpy.

As used herein, 'β-alanine' refers to the chemical beta-alanine, also known as 3-aminopropionic acid. Additionally, as used herein, 'β-alanine' also includes derivatives of β-alanine such as esters, amides, and salts, as well as other derivatives, including derivatives having pharmacoproperties upon metabolism to an active form.

As used herein, 'malic acid' refers to the chemical 1-Hydroxy-1,2-ethanedicarboxylic acid, (CAS Registry No. 6915-15-17), also known as, hydroxybutanedioic acid, hydroxysuccinic acid, malate, or 2-hydroxybutanedioate. Additionally, as used herein, 'malic acid' also includes derivatives of malate such as esters, amides, and salts, as well as other derivatives, including derivatives having pharmacoproperties upon metabolism to an active form.

As used herein, 'citric acid' refers to the chemical 2-hydroxy-1,2,3-propane-tricarboxylic acid, (CAS Registry No. 77-92-9), also known as, β-hydroxytricarboxylic acid. Additionally, as used herein, 'citric acid' also includes derivatives of citrate such as esters, amides, and salts, as well as other derivatives, including derivatives having pharmacoproperties upon metabolism to an active form.

As used herein, 'fumaric acid' refers to the chemical (E)-2-butenedioic acid, (CAS Registry No. 110-17-8), also known as, trans-1,2-ethylenedicarboxylic acid, allomaleic acid, and boletic acid. Additionally, as used herein, 'fumaric acid' also includes derivatives of fumarate such as esters, amides, and salts, as well as other derivatives, including derivatives having pharmacoproperties upon metabolism to an active form.

As used herein, the term 'organic acid' refers to organic compounds which contain carboxylic acids (—C(O)OH). Typical examples of organic acids include, but are not limited to; malic acid, fumaric acid, citric acid, orotic acid, lactic acid, pyruvic acid, and tartaric acid.

As used herein, the term 'pharmaceutically acceptable excipients' refers to substances added to produce quality tablets, chewable tablets, capsules, granulates or powders, but which do not provide nutritive value. A non-exhaustive list of examples of excipients includes monoglycerides, magnesium stearate, modified food starch, gelatin, microcrystalline cellulose, glycerin, stearic acid, silica, yellow beeswax, lecithin, hydroxypropylcellulose, croscarmellose sodium, and crosprovidone.

According to the present invention, the compounds disclosed herein comprise molecules of β-alanine combined with an organic acid to form a salt having a structure according to Formula 1. The aforementioned compound being prepared according to the reaction as set forth for the purposes of the description in Scheme 1:

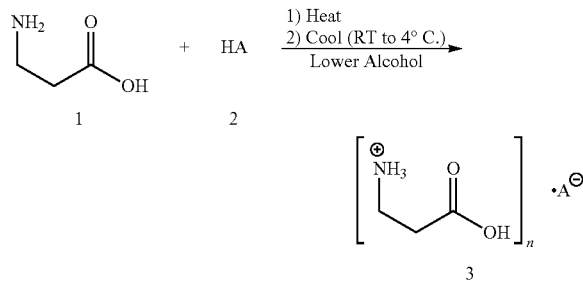

With reference to Scheme 1, in the first step of the reaction the β-alanine (1) is dissolved in an excess of hot lower alcohol. The lower alcohol is considered to be hot, as would be known by one of ordinary skill in the art. Preferably the lower alcohol is considered to be hot when heated to a temperature about 5° C. below the boiling point of the corresponding lower alcohol.

In various embodiments of the present invention, the lower alcohol is selected from the group consisting of methanol, ethanol, propanol, and isopropanol. These lower alcohols may be used singly or in admixture containing two or more alcohols.

Concurrently, in the second step of the reaction the organic acid (2) is dissolved into an excess of hot lower alcohol. The lower alcohol is considered to be hot, as would be known by one of ordinary skill in the art. Preferably the lower alcohol is considered to be hot when heated to a temperature about 5° C. below the boiling point of the corresponding lower alcohol.

Both solutions above are then mixed together and heated to about the boiling point of the corresponding lower alcohol. If there are solids still present after heating, the solution is filtered while hot to remove any unreacted starting materials. The solution is then allowed to cool to room temperature, covered and refrigerated or cooled until crystallization occurs, preferably for between about 24 to about 48 hours. The resultant crystals are filtered under vacuum and washed with ice cold lower alcohol, yielding a crystalline powder, the β-alanine organic acid salt (3).

In larger scale preparations of the present invention, diethyl ether can be added until the cloud point, as would be known to one of skill in the art, is reached after the mixture is cooled to room temperature, after which the solution is refrigerated or cooled to allow crystallization to complete. This will facilitate greater precipitation of the product thus yielding more of the β-alanine organic acid salt (3), which would be desired in industrial settings.

β-alanine organic acid salts are used advantageously alone or with additional active ingredients, such as, trace elements, vitamins, mineral substances, or other amino acids as well as, optionally, excipients usually used for the preparation of the respective forms of administration. The forms of administration include, particularly, all varieties of tablets, both those that are swallowed without being chewed, and tablets to be chewed or dissolved in the mouth of an individual, as well as those that are dissolved in a liquid before being ingested by an individual. The tablet forms include uncoated tablets, one-layer or multilayer or encased forms or effervescent tablets. Further preferred forms of administration are capsules of hard and soft gelatin, the latter being particularly suitable to include a liquid core. Additionally, β-alanine organic acid salts can be used advantageously for the preparation of solutions and suspensions and as a powder, either effervescent or granulated.

The examples given below explain the execution of the invention with respect to the production of β-alanine organic acid salts. Provided below is a basic method for producing β-alanine organic acid salts. However, those of skill in the art will appreciate certain changes may be made in the process of "scaling-up" the reaction to manufacture larger batches of β-alanine organic acid salts which may be required for commercial uses and supply requirements. Other methods of synthesis may also be apparent to those of skill in the art.

EXAMPLES

Example 1

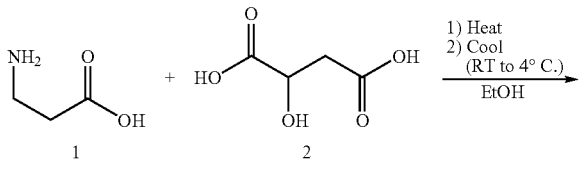

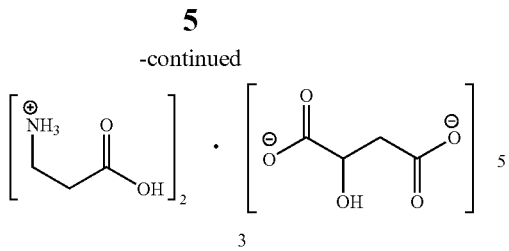

178.18 g (2 mol) of β-alanine (1) is dissolved into 400 mL of hot ethanol, solution 1. Concurrently, 134.09 g (1 mol) of malic acid (2) is dissolved in 200 mL of hot ethanol, solution 2. Solution 2 is added to solution 1 with stirring and the resultant solution is heated to the boiling point. If there are solids still present the solution is filtered at this temperature to remove unreacted starting materials. The solution is then allowed to cool to room temperature and then covered and refrigerated to allow crystallization to complete; about 24 hours. The resultant crystals are filtered under vacuum and washed with ice cold ethanol, yielding a crystalline powder, the β-alanine malate (3).

Example 2

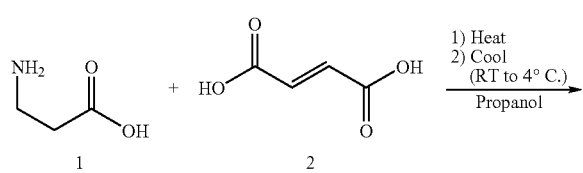

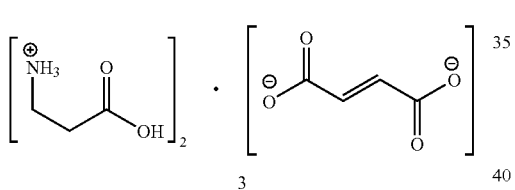

178.18 g (2 mol) of β-alanine (1) is dissolved into 400 mL of hot propanol, solution 1. Concurrently, 116.07 g (1 mol) of fumaric acid (2) is dissolved in 200 mL of hot propanol, solution 2. Solution 2 is added to solution 1 with stirring and the resultant solution is heated to the boiling point. If there are solids still present the solution is filtered at this temperature to remove unreacted starting materials. The solution is then allowed to cool to room temperature and refrigerated to allow crystallization to complete; about 24 hours. The resultant crystals are filtered under vacuum and washed with ice cold ethanol, yielding a crystalline powder, the β-alanine fumarate (3).

Example 3

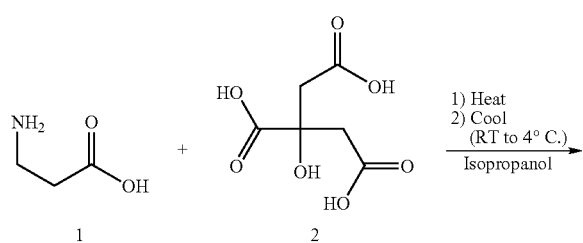

267.27 g (3 mol) of β-alanine (1) is dissolved into 600 mL of hot isopropanol, solution 1. Concurrently, 192.12 g (1 mol) of citric acid (2) is dissolved in 300 mL of hot isopropanol, solution 2. Solution 2 is added to solution 1 with stirring and the resultant solution is heated to the boiling point. If there are solids still present the solution is filtered at this temperature to remove unreacted starting materials. The solution is then allowed to cool to room temperature and refrigerated to allow crystallization to complete; about 24 hours. The resultant crystals are filtered under vacuum and washed with ice cold ethanol, yielding a crystalline powder, the β-alanine citrate (3).

Extensions and Alternatives

In the foregoing specification, the invention has been described with a specific embodiment thereof; however, it will be evident that various modifications and changes may be made thereto without departing from the broader spirit and scope of the invention.

What is claimed:

1. A salt of β-alanine and an organic acid, having the general formula:

$$\left[ \begin{array}{c} \overset{\oplus}{NH_3} \\ \phantom{xx} \\ \phantom{xx}OH \end{array} \right]_n \cdot A^{\ominus}$$

wherein:
A⁻ represents a deprotonated organic acid selected from the group consisting of: orotic acid, and pyruvic acid; and
n=1.

2. A composition comprising the salt of β-alanine and an organic acid of claim 1, wherein the composition further comprises pharmaceutically acceptable excipients.

3. The composition of claim 2 wherein the pharmaceutically acceptable excipients are selected from the group consisting of monoglycerides, magnesium stearate, modified food starch, gelatin, microcrystalline cellulose, glycerin, stearic acid, silica, yellow beeswax, lecithin, hydroxypropylcellulose, croscarmellose sodium, and crosprovidone.

4. The salt of β-alanine and an organic acid of claim 1 wherein said salt is provided in a dosage form selected from the group consisting of tablets, chewable tablets, capsules, granulates and powders.

5. The composition of claim 2 wherein the composition is provided in a dosage form selected from the group consisting of tablets, chewable tablets, capsules, granulates and powders.

6. The salt of β-alanine and an organic acid of claim 4 wherein said salt is administered to a mammal.

7. The composition of claim 5 wherein the composition is administered to a mammal.

8. The composition of claim 1, wherein the deprotonated organic acid is orotic acid.

9. The composition of claim 1, wherein the deprotonated organic acid is pyruvic acid.

10. The composition of claim 2, wherein the deprotonated organic acid is orotic acid.

11. The composition of claim 2, wherein the deprotonated organic acid is pyruvic acid.

12. The composition of claim 5, wherein the deprotonated organic acid is orotic acid.

13. The composition of claim 5, wherein the deprotonated organic acid is pyruvic acid.

* * * * *